United States Patent [19]

Burkhart

[11] Patent Number: 5,951,559
[45] Date of Patent: Sep. 14, 1999

[54] METHOD FOR INSTALLING A THREADED SUTURE ANCHOR WITH A CANNULATED SUTURE ANCHOR DRILL GUIDE

[75] Inventor: Stephen S. Burkhart, San Antonio, Tex.

[73] Assignee: Arthrex, Inc., Naples, Fla.

[21] Appl. No.: 08/893,489

[22] Filed: Jul. 11, 1997

Related U.S. Application Data

[60] Provisional application No. 60/023,088, Jul. 25, 1996.

[51] Int. Cl.⁶ .................................................. A61B 17/56
[52] U.S. Cl. ............................... 606/73; 606/96; 606/104
[58] Field of Search ............................... 606/96, 104, 97, 606/98, 99, 88, 86, 73, 232

[56] References Cited

U.S. PATENT DOCUMENTS

| | | | |
|---|---|---|---|
| 5,662,658 | 9/1997 | Wenstrom, Jr. ......................... | 606/104 |
| 5,681,333 | 10/1997 | Burkhart et al. ........................ | 606/148 |
| 5,683,401 | 11/1997 | Schmieding et al. .................... | 606/104 |
| 5,700,266 | 12/1997 | Harryman, II ............................ | 606/80 |

*Primary Examiner*—Guy V. Tucker
*Attorney, Agent, or Firm*—Ostrolenk, Faber, Gerb & Soffen, LLP

[57] ABSTRACT

An arthroscopic method and apparatus for implanting a suture anchor into tissue using a cannulated drill guide having an indented tip. Ligament tissue at a shoulder repair site is penetrated with a cannulated drill guide and removable trochar obturator. The obturator is removed, and the indented tip is positioned to straddle the glenoid rim at the repair site. Suture material is appended to a suture anchor. The pre-threaded suture anchor is attached to a device driver and installed through the cannulated drill guide into the repair site, by turning into bone.

5 Claims, 7 Drawing Sheets

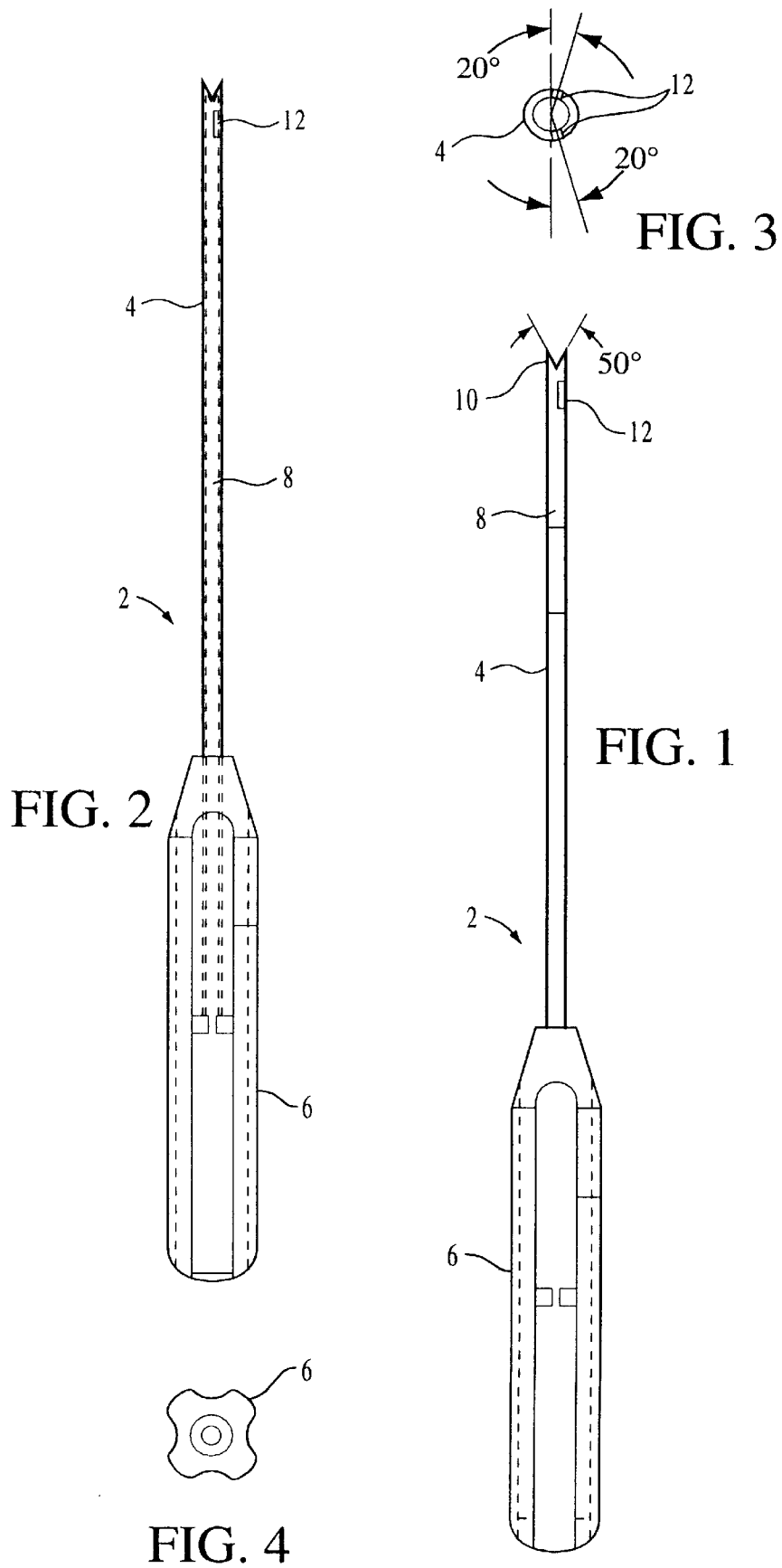

METHOD FOR INSTALLING A THREADED SUTURE ANCHOR WITH A CANNULATED SUTURE ANCHOR DRILL GUIDE

This application claims the benefit of U.S. Provisional Application Ser. No. 60/023,088, filed Jul. 25, 1996.

BACKGROUND OF THE INVENTION

1. Field of the Invention

The present invention relates to an arthroscopic surgical method and apparatus for suture fixation and, more specifically, to an arthroscopic method and apparatus for performing anatomic ligament repair using suture anchors installed through a thin, cannulated, open-section drill guide.

2. Brief Description of the Prior Art

Suture anchors are used in arthroscopic surgery to secure suture material to tissue. Various suture anchor assemblies have been developed. For example, U.S. Pat. Nos. 4,632,100 to Somers et al. and 4,898,156 to Gatturna et al. disclose suture anchors and tools for suture anchor installation. See also U.S. Pat. No. 4,899,743 to Nicholson et al.

Guiding small suture anchor pins while accurately positioning repair tissue and driving the suture anchors into bone can be excessively demanding. For example, in arthroscopic Bankart repair, inserting suture anchors into the glenoid rim is technically formidable, making the procedure very difficult.

Improved methods and apparatus also are needed for performing other surgical procedures, especially arthroscopic procedures, such as labral reconstructions, including superior labral anterior to posterior (SLAP) lesion repairs, as well as in knee and other joint surgery, for example, primary anterior cruciate ligament (ACL) repairs.

Repositioning and securing of the tissue to be sutured is provided by the inventions of U.S. Pat. No. 5,683,401, and U.S. Pat. No. 5,466,243, having common assignment with the present application, the disclosures of which are incorporated herein by reference.

Pursuant to the methods noted above, once the ligament has been speared and mobilized into position at the repair site, the suture anchor is driven through the ligament and into bone.

The need exists for arthroscopic instruments and methods that mobilize and spear the ligament and provide a secure platform for inserting the suture anchor into bone. Such a technique would securely place the anchor into bone and the sutures through the ligament as a single step.

SUMMARY OF THE INVENTION

The present invention provides a method and apparatus for inserting and installing suture anchors through a thin, cannulated drill guide. The drill guide has an indented guide tip at the distal end of the cannula that straddles, for example, the corner of the glenoid rim, to secure the drill guide as the suture anchor is installed into the bone with a suture anchor driver. An open section in the cannula allows visualization during installaion of both the suture anchor and a laser mark, located on the suture anchor driver, that serves as a depth stop.

According to a preferred operative procedure of the present invention, an arthroscopic elevator is used initially to free any adhesions between the glenohumeral ligaments and bone in preparation for the anatomic repair of the ligaments. The drill guide of the present invention, provided with a trochar obturator, penetrates, for example, the inferior glenohumeral ligament in preparation for shifting the ligament to the glenoid where the ligament will be secured.

Once the ligament or tissue has been penetrated, the obturator is backed away from the drill guide tip. The indented tip of the drill guide is placed so that the indentation straddles the corner of the glenoid rim. The obturator is replaced within the drill guide by a suture anchor and driver assembly, the suture anchor and driver assembly preferably having been pre-threaded with suture. The driver is used to installed the suture anchor into the bone.

During installation the open section in the drill guide allows visualization of the suture anchor and a laser mark, located on the side of the suture anchor driver, that serves as a depth stop. The laser mark can be located on the driver such that, when the mark approaches the distal end of the open section in the cannula, the suture anchor has been inserted to the correct depth, preferably to where the proximal end of the suture anchor is flush with the bone surface.

As a result of installing the threaded suture anchor into the glenoid rim, the suture anchor and the suture are inserted through the ligament and bone in one step, eliminating the need for suture passers to take the suture through the ligament as an additional step.

A crochet hook is used to retrieve one limb of the suture so that a simple knot can be used to tie down the ligament to the bone, with the two limbs of the suture surrounding the intervening ligamentous tissue. A knot pusher, such as that disclosed in U.S. application Ser. No. 08/745,189, filed Nov. 7, 1996, by the present applicant, is used to tie the ligamentous tissue securely to the bone. The entire procedure is repeated with additional suture anchors as needed. Two or three anchors usually are sufficient.

According to a preferred embodiment, the drill guide has two open sections located on either side of the cannulated drill guide. The open sections allow the instrument to be used in performing right or left shoulder repairs. The windows preferably are positioned at 20° above a center line drawn across the cannulated guide for ease of viewing. Accordingly, the windows are separated by 140°.

The present invention also can be used for performing other surgical procedures, especially arthroscopic procedures, such as labral reconstructions, including SLAP lesion repairs, as well as in knee and other joint surgeries, for example, primary anterior cruciate ligament (ACL) repairs.

Other features and advantages of the present invention will become apparent from the following description of the invention which refers to the accompanying drawings.

BRIEF DESCRIPTION OF THE DRAWINGS

FIG. 1 is a side view of the thin, cannulated drill guide of the present invention.

FIG. 2 is a sectional side view of the cannulated drill guide of the present invention.

FIG. 3 is a partial, distal end view of the drill guide of the present invention.

FIG. 4 is a partial, proximal end view according to the guide according to the present invention.

DETAILED DESCRIPTION OF THE PREFERRED EMBODIMENT

Figure 5:
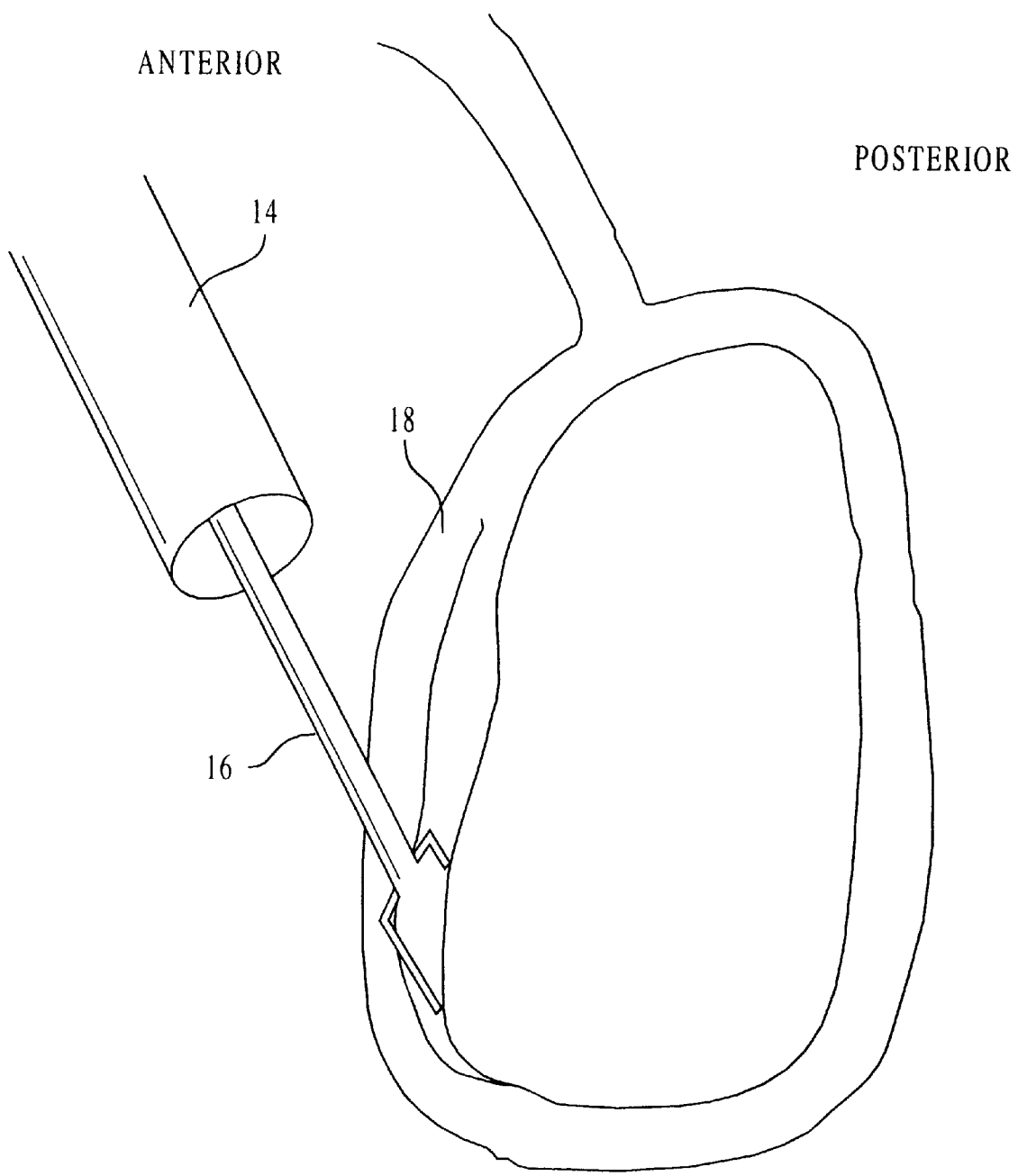
FIG. 5 is a schematic view of a method step of preparing a site for anatomic repair according to the present invention.

Referring to FIGS. 1 and 2, the present invention relates to a cannulated drill guide 2 consisting of a cannulated shaft 4 secured to a handle 6.

Guide 2 has a central cannula 8 that extends through shaft 4 and handle 6 for receiving a suture anchor driver, as described in more detail below. A V-shaped guide tip 10 and an open side window 12 are formed on the distal end of shaft 4.

FIG. 3 is an end view of guide tip 10. As shown in FIG. 4; the V-shaped tip 10 is formed by a notch having an angle of preferably 50°. The V-shaped configuration of the guide tip sits precisely onto the rim of the glenoid for accurate, anatomical screw placement.

Referring also to FIG. 3, window 12 is formed as an oval opening in cannula 4. Preferably, two windows are formed on opposite sides of cannula 4, each at an angle of preferably 20° from the horizontal. FIG. 4 is a proximal end view of the cannulated handle of the present invention.

Referring to FIG. 5, a preferred method of installing suture anchors in accordance with the present invention is shown. An anterior portal is provided with a cannula 14. Alternatively, in certain surgical applications, the obturated drill guide itself can be used to create a portal and function as a cannula.

An arthroscopic elevator 16 is used to free any adhesions between the glenohumeral ligaments 18 and the bone in preparation for anatomic repair of the ligaments.

Figure 6:
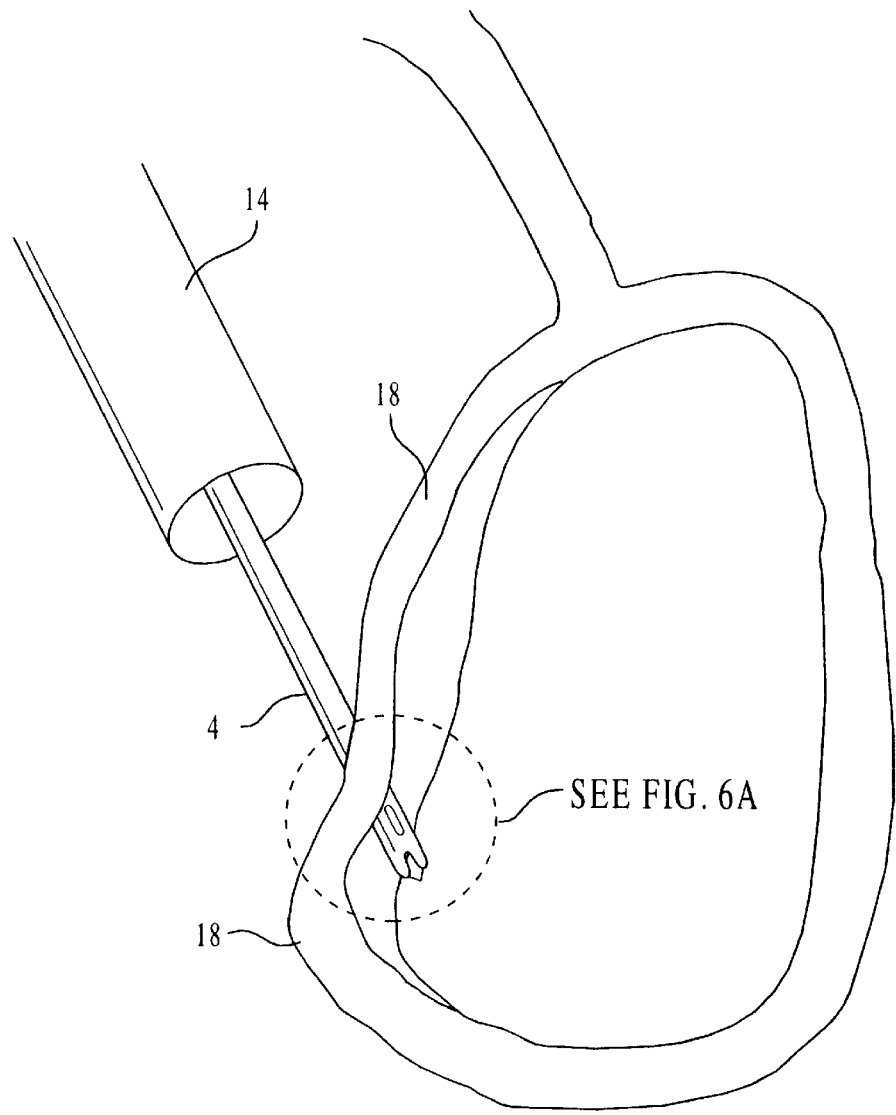
FIG. 6 is a schematic view of a method step of penetrating the inferior glenohumeral ligament with the drill guide according to the present invention.
Figure 6A:
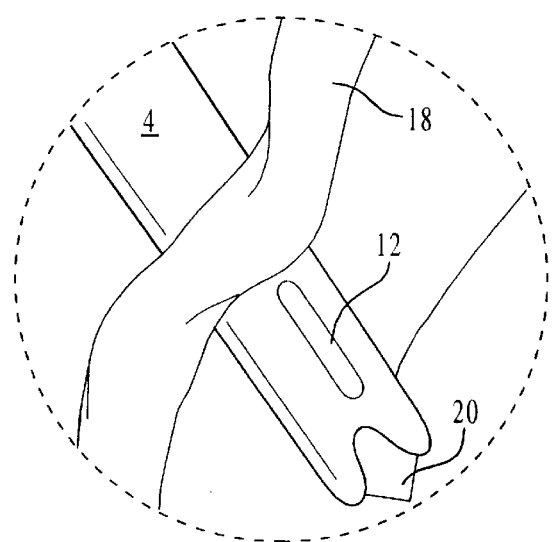
FIG. 6A is an enlarged schematic view showing the open section and trochar obturator according to the method step of FIG. 6.

Referring to FIGS. 6 and 6A, the drill guide 2 is held in one hand using handle 6 (not shown) and is inserted through cannula 14 into the surgical site, approaching the area to be repaired with indented tip 10. A trochar obturator 20 is provided within the thin cannula 4. The thin cannula with its trochar penetrate the inferior glenohumeral ligament 18 in preparation for shifting the ligament to the glenoid rim where it will be secured by suture anchors.

Once the ligament has been penetrated, the obturator is retrograded, and the drill guide is placed so that the indentation 10 straddles the corner of the glenoid rim.

Figure 7:
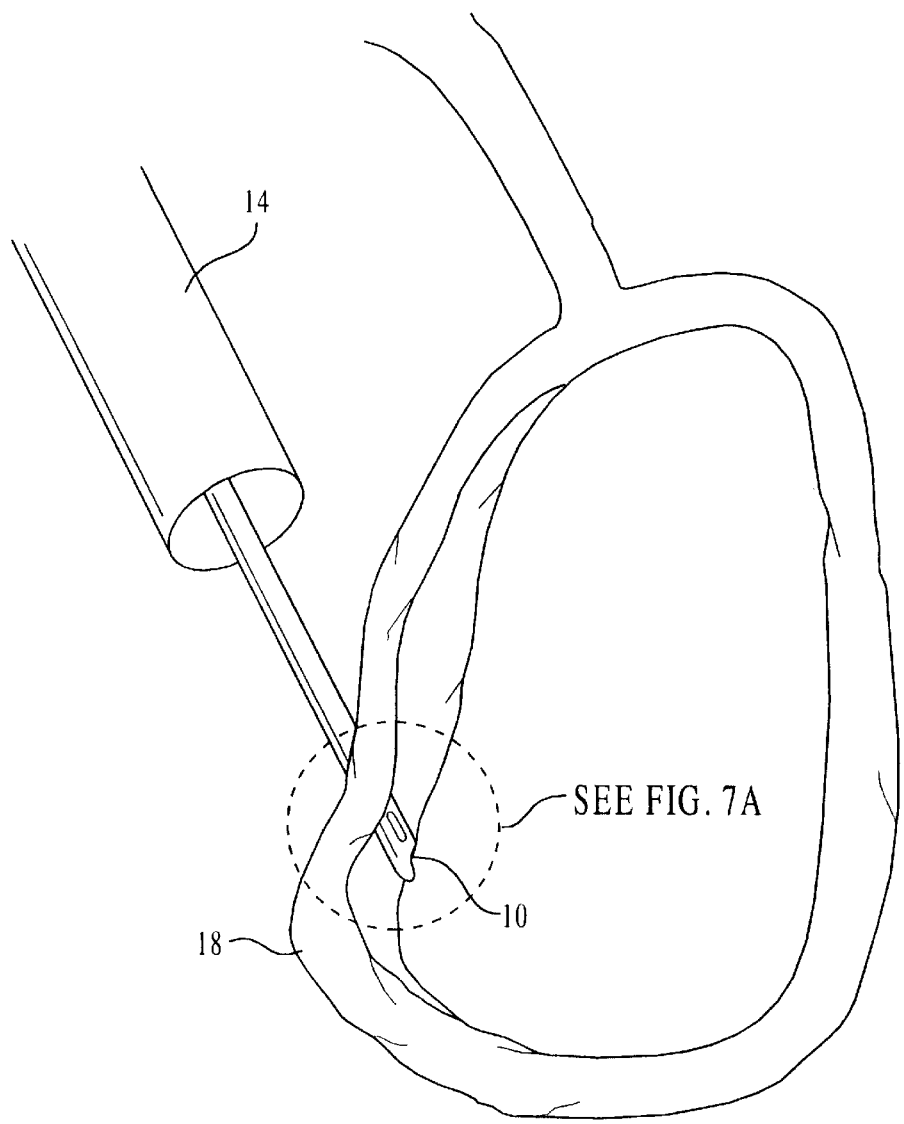
FIG. 7 is a schematic view of a method step of straddling the glenoid rim with the drill guide according to the present invention.
Figure 7A:
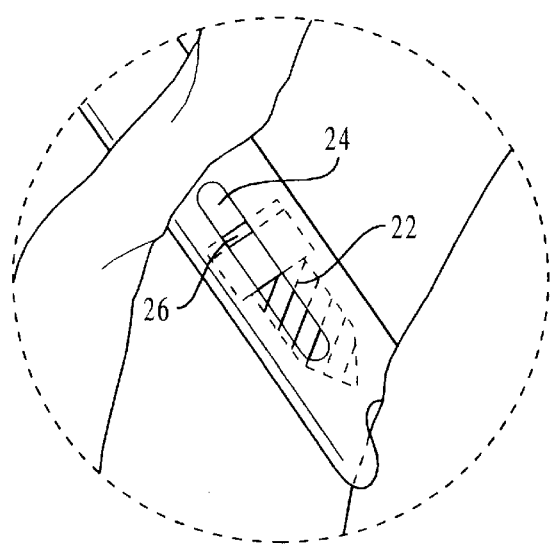
FIG. 7A is an enlarged schematic view showing the suture anchor and driver within the indented guide tip according to the method step of FIG. 7.

Referring to FIGS. 7 and 7A, the obturator is replaced within the drill guide by a suture anchor and driver assembly. Prior to insertion, suture anchor 22 and suture anchor driver 24 are pre-threaded with suture. Driver 24 is provided with a laser mark 26 that acts as a depth stop and can be viewed through open section 12 in the cannula as the suture anchor is installed into the glenoid.

To thread the suture anchor prior to insertion, appropriately sized suture is threaded through an eye of the suture anchor. The eye and drive end of suture anchor 22 are seated in device driver 26. A threading device such as shown in U.S. Pat. No. 5,466,243 may be used to thread the suture through the device driver.

A laser mark also can be formed on the proximal end of the inserter to correspond with the depth of the end of the suture anchor eyelet for direct visualization of insertion depth during arthroscopic and open procedures done in conjunction with the guide of the present invention.

Figure 8:
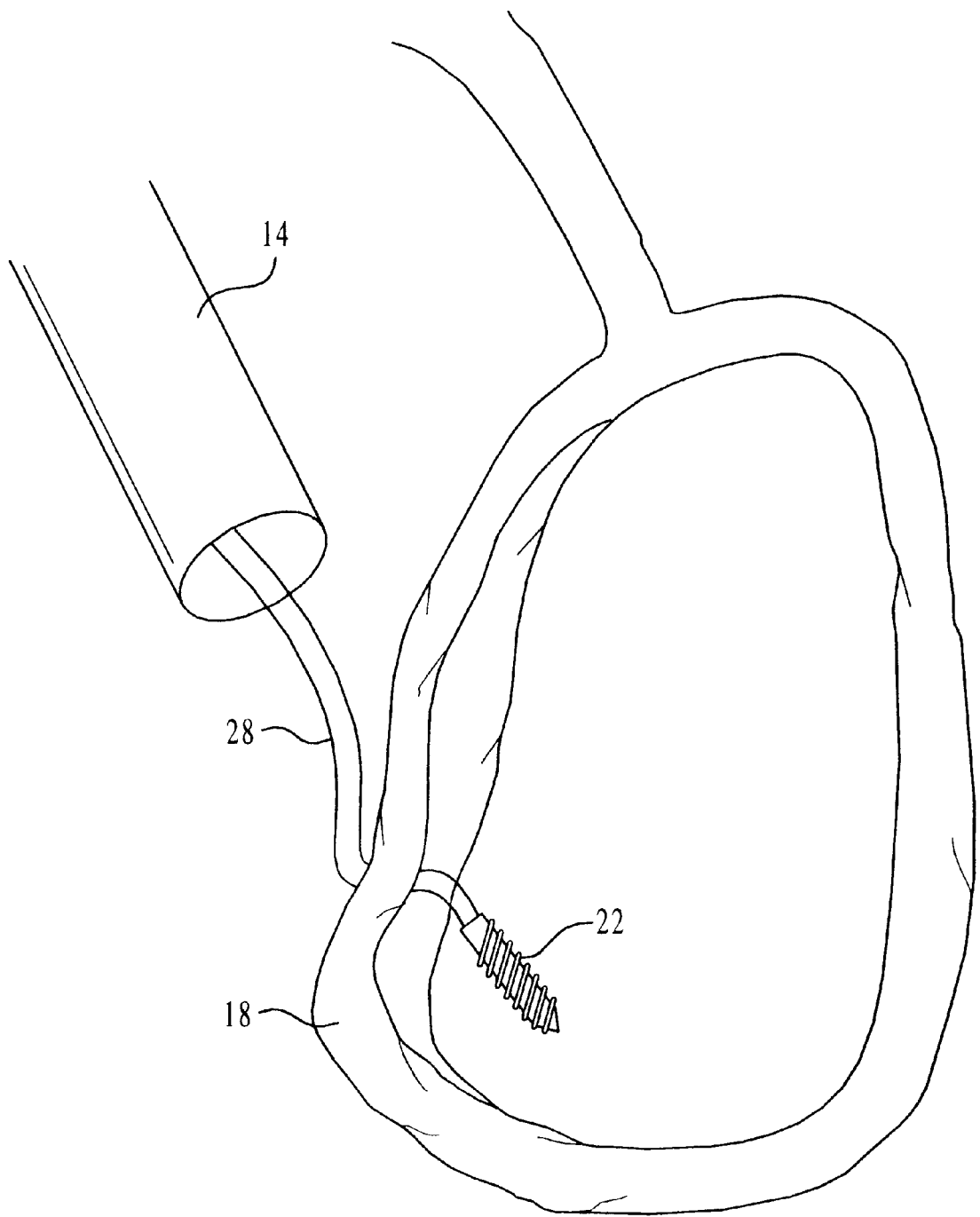
FIG. 8 is a schematic view of a method step after insertion of a threaded suture anchor according to the present invention.

Once suture anchor 22 is in place, device driver 24 and cannulated drill guide 2 are withdrawn from the repair site. See FIG. 8. The threaded suture anchor 22 has been inserted through the ligament and into the bone in one step, eliminating the need for suture passers to take the suture 28 through the ligament as an additional step.

Figure 9:
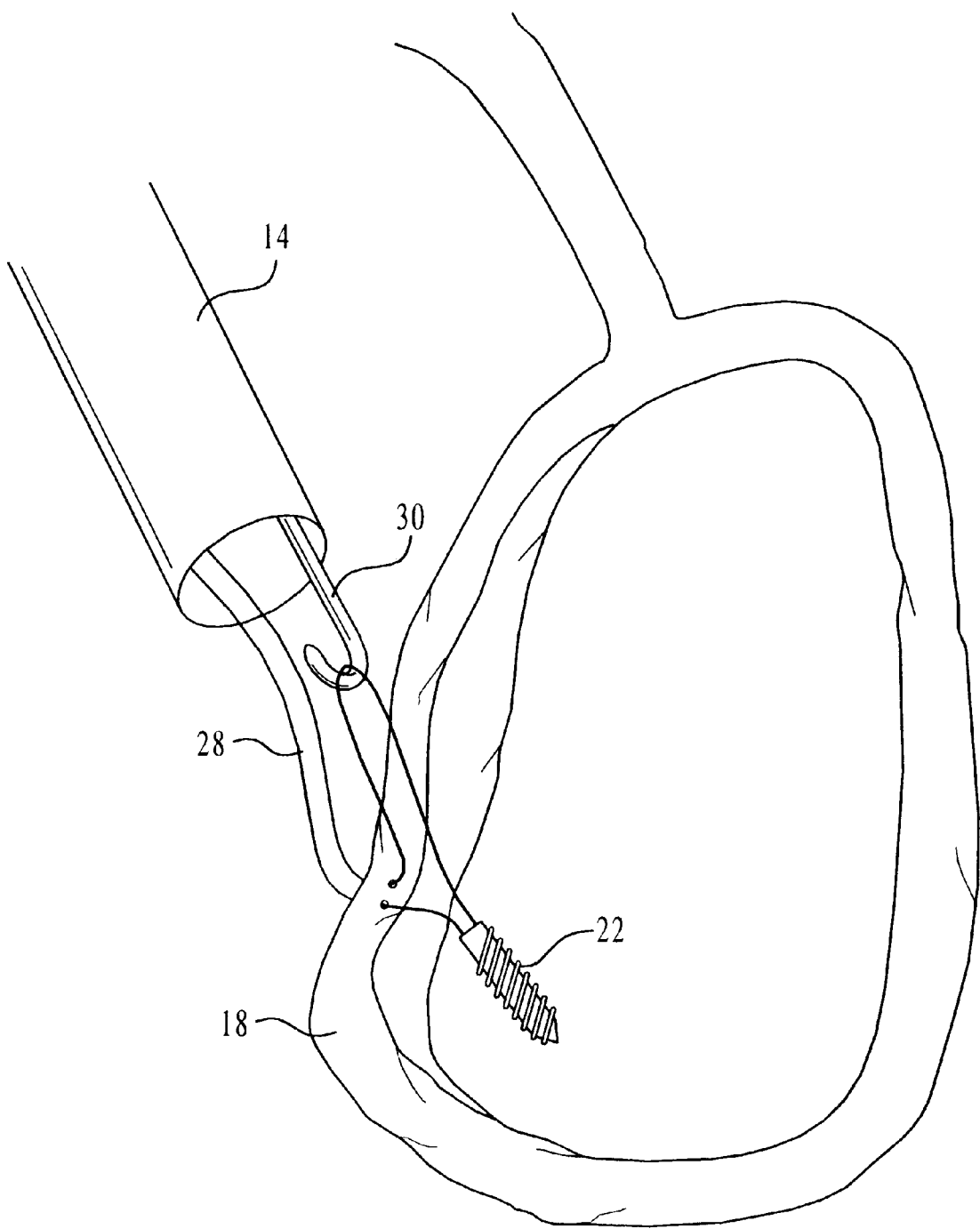
FIG. 9 is a schematic view of a method step of retrieving a suture limb using a crochet hook according to the present invention.

Referring to FIG. 9, a crochet hook 30 retrieves one limb of the suture so that a simple knot can be used to tie the ligament down to the bone, with the two limbs of the suture surrounding the intervening ligamentous tissue.

Figure 10:
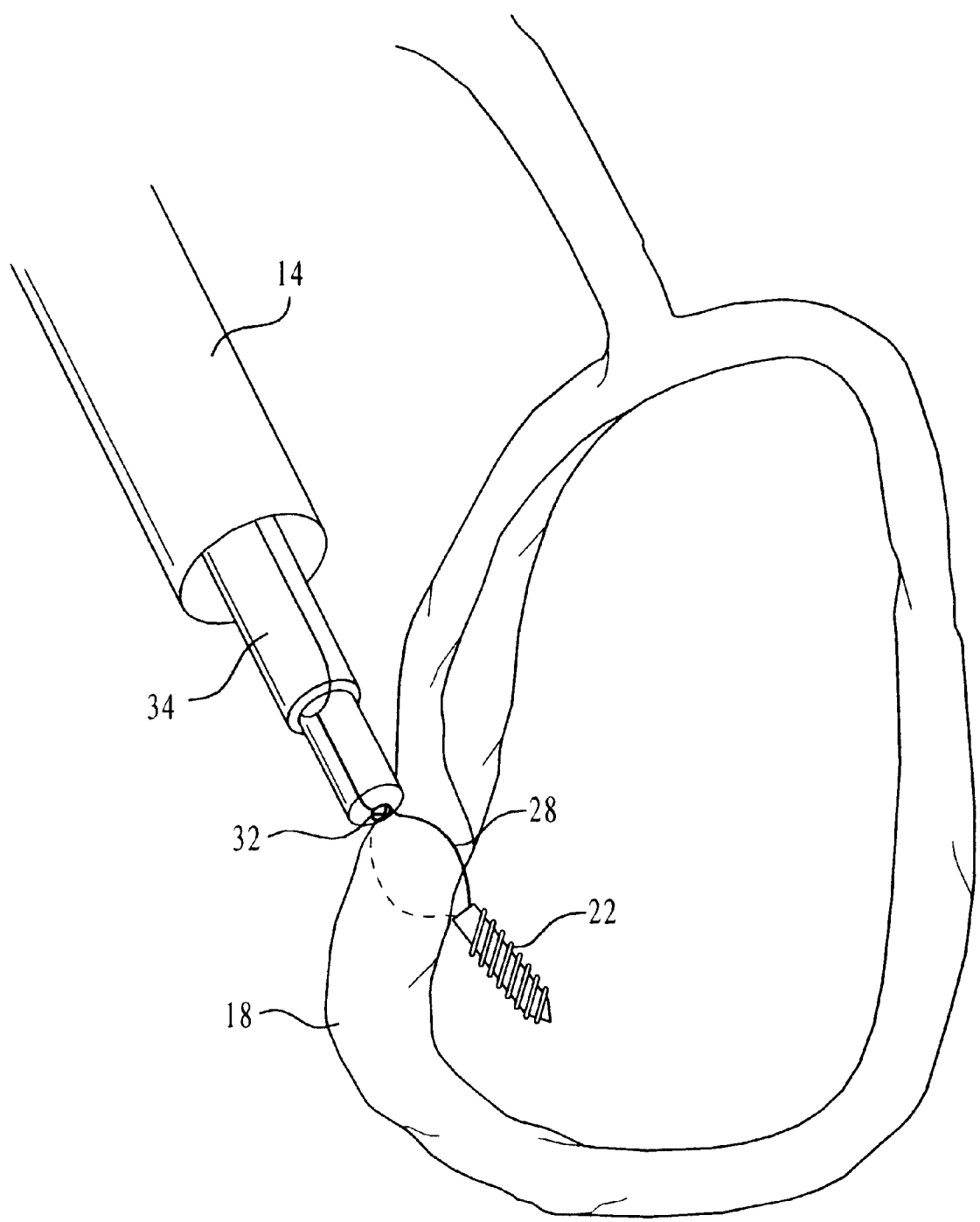
FIG. 10 is a schematic view of a method step using a knot pusher according to the present invention.

As shown in FIG. 10, knots 32 in the suture material are tied using a knot pusher 34 such as that described in U.S. Pat. No. 5,176,691. The installation procedure is repeated as necessary to install additional suture anchors. Two or three anchors usually are sufficient. Tissue may be subsequently secured with free needles using standard open Bankart repair techniques.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A method for installing a threaded suture anchor for securing tissue to bone using a cannulated drill guide having a tip provided with an indent for straddling a bone ridge, the method comprising the steps of:

(a) inserting an obturator into the cannulated drill guide so that the obturator protrudes from the tip;

(b) penetrating the tissue with the drill guide;

(c) retracting the obturator from the drill guide tip;

(d) advancing the tip of the drill guide such that it straddles the bone ridge;

(e) inserting the threaded suture anchor and a driver into the drill guide;

(f) inserting the suture anchor into the bone by turning the suture anchor with the driver; and (g) removing the cannulated drill guide and driver from the repair site, leaving the threaded suture anchor installed in the bone.

2. The method of claim 1, wherein in the step of inserting the suture anchor into bone, the suture anchor is inserted to a depth of insertion determined by a calibrated laser mark on the driver.

3. The method of claim 1, wherein the drill guide includes an open section near the distal end of the drill guide, the method further comprising the step of viewing the suture anchor and driver through the open section as they pass through the cannulated drill guide.

4. The method of claim 1, wherein the bone ridge is the glenoid rim.

5. The method of claim 1, wherein the threaded suture anchor is loaded with suture prior to insertion into the drill guide.

* * * * *